(12) United States Patent
Vaccaro et al.

(10) Patent No.: US 7,253,908 B2
(45) Date of Patent: Aug. 7, 2007

(54) NON-DESTRUCTIVE INSPECTION USING LASER PROFILING AND ASSOCIATED METHOD

(75) Inventors: Christopher M. Vaccaro, O Fallon, MO (US); Roger W. Engelbart, St. Louis, MO (US); Nancy L. Wood, Clayton, MO (US)

(73) Assignee: The Boeing Company, Chicago, IL (US)

( * ) Notice: Subject to any disclaimer, the term of this patent is extended or adjusted under 35 U.S.C. 154(b) by 445 days.

(21) Appl. No.: 10/897,272

(22) Filed: Jul. 22, 2004

(65) Prior Publication Data

US 2006/0017937 A1 Jan. 26, 2006

(51) Int. Cl.
*G01B 11/24* (2006.01)
*G06K 9/00* (2006.01)

(52) U.S. Cl. ..................................... 356/607; 382/141

(58) Field of Classification Search .. 356/237.1–237.5, 356/607–608, 614–615, 625, 601; 382/8, 382/18, 55, 286, 149, 141
See application file for complete search history.

(56) References Cited

U.S. PATENT DOCUMENTS

| | | | | |
|---|---|---|---|---|
| 4,470,122 A * | 9/1984 | Sarr | ........................... | 702/150 |
| 4,561,776 A * | 12/1985 | Pryor | ........................... | 356/72 |
| 4,591,996 A | 5/1986 | Vachon | | |
| 4,774,842 A | 10/1988 | Kollar et al. | | |
| 5,331,169 A * | 7/1994 | Tanaka et al. | ............... | 250/372 |
| 5,379,347 A * | 1/1995 | Kato et al. | .................... | 382/141 |
| 5,567,881 A | 10/1996 | Myers | | |
| 5,671,042 A * | 9/1997 | Sciammarella | .............. | 356/35.5 |
| 5,698,787 A | 12/1997 | Parzuchowski et al. | | |
| 5,824,908 A | 10/1998 | Schindel et al. | | |
| 5,825,495 A * | 10/1998 | Huber | ......................... | 356/600 |
| 6,118,540 A * | 9/2000 | Roy et al. | .................... | 356/394 |
| 6,438,272 B1* | 8/2002 | Huang et al. | ................ | 382/286 |
| 6,525,810 B1* | 2/2003 | Kipman | .................... | 356/237.1 |
| 6,591,679 B2* | 7/2003 | Kenefick et al. | ............... | 73/597 |
| 6,637,266 B1 | 10/2003 | Froom | | |
| 6,678,403 B1 | 1/2004 | Wilk | | |
| 6,871,684 B2* | 3/2005 | Engelbart et al. | ............ | 156/361 |
| 6,937,758 B2* | 8/2005 | Keithley | ...................... | 382/167 |
| 2003/0191603 A1 | 10/2003 | Raab et al. | | |
| 2004/0076322 A1* | 4/2004 | Guetta | ......................... | 382/145 |

* cited by examiner

*Primary Examiner*—Sang H. Nguyen
(74) *Attorney, Agent, or Firm*—Alston & Bird LLP

(57) ABSTRACT

A system for non-destructive inspection using laser profiling and an associated method are provided. The system includes a support surface, and at least one laser carried by the support surface and directed towards the workpiece at an oblique angle such that at least a portion of the workpiece is illuminated by the laser. The system also includes a camera carried by the support surface and capable of capturing reflections from the workpiece, as well as a translation device capable of traveling proximate to the workpiece. The support surface is coupled to the translation device such that the laser and the camera are capable of traveling along the workpiece. The system further includes a data acquisition system capable of communicating with the camera such that the data acquisition system creates an image indicative of at least a portion of the workpiece based on the reflections from the workpiece.

21 Claims, 4 Drawing Sheets

NON-DESTRUCTIVE INSPECTION USING LASER PROFILING AND ASSOCIATED METHOD

BACKGROUND OF THE INVENTION

1) Field of the Invention

The present invention relates to non-destructive inspection and, more particularly, to non-destructive inspection of a workpiece using laser profiling, as well as an associated method.

2) Description of Related Art

Non-destructive testing of structures involves thoroughly examining a structure without harming, or requiring significant disassembly of, the structure. Non-destructive testing is advantageous for many applications in which a thorough inspection of the exterior and/or interior of a structure is required. For example, non-destructive testing is commonly utilized in the aircraft industry to inspect aircraft structures for any type of internal or external damage to the structure. Metallic aircraft structures are typically inspected for corrosion and/or cracking, particularly near fasteners in the structure. Composite structures are typically inspected for any type of damage, such as delamination, occurring anywhere on or within the composite material.

Various types of sensors may be utilized to perform non-destructive testing. One or more sensors may move over the portion of the structure to be examined, and receive data regarding the structure. For example, ultrasonic testing could be used to generate a sound wave through a sensor or probe that is directed towards a part. When there is a flaw in the part, part of the sound wave will reflect back from the flaw and will be detected. A pulse-echo sensor may be utilized to obtain ultrasonic data, such as thickness gauging, detection of laminar defects and porosity, and/or crack detection in the structure. Resonance, pitch/catch or mechanical impedance sensors may be utilized to provide indications of voids or porosity, such as in adhesive bondlines of the structure. In addition, single and dual frequency eddy current probes, utilizing electromagnetic induction, impart and detect eddy currents within a structure so as to identify cracks and/or corrosion, particularly in metallic or other conductive structures. The data acquired by the sensors is typically processed by a processing element, and the processed data may be presented to a user via a display.

Once a defect is located on a part, the part may be repaired or replaced. If the part is to be repaired, the defect is typically machined (e.g., grinding), which requires an additional inspection to determine the amount of material removed to assess the load-carrying capability of the machined part. Generally, a feeler gauge or ultrasonic time-of-flight methods are used to inspect the machined part. Inspecting with feeler gauges are time consuming, lack useful output for analysis, and are prone to human error. Using ultrasonic time-of-flight inspection is more efficient and reliable than inspecting with a feeler gauge, but ultrasonic inspection utilizes a sensor that is much larger than the size of the grind-out area removed during machining.

Current portable inspection systems may be automatic or manual. For example, automatic scanners such as the Mobile Automated Scanner (MAUS®) system, developed by The Boeing Company, are proficient in inspecting relatively flat parts such as wing and fuselage skins. One type of MAUS® system automatically moves along the structure via a track with strategically controlled suction cups, while another type includes handheld sensors and an associated carriage that is moved along the structure via manual motion. As such, the MAUS® system not only scans the part, but also processes the data regarding the structure, and associates the data with the exact location on the part from where the data was obtained. The data is used to create C-scans and B-scans so that flaws or other items of interest may be detected on the surface of the part.

It would therefore be advantageous to provide an inspection system capable of inspecting a workpiece that is accurate and reliable. Also, it would be advantageous to provide an inspection system that is capable of generating images depicting a surface profile of the workpiece. Finally, it would be advantageous to provide a portable inspection system capable of inspecting portions of interest on a workpiece efficiently.

BRIEF SUMMARY OF THE INVENTION

The invention addresses the above needs and achieves other advantages by providing an inspection system capable of generating a surface contour of the workpiece. The inspection system employs a translation device in conjunction with a laser and camera such that the laser and camera may move along the workpiece while generating and capturing data indicative of the workpiece. The data generated may then be used to create an image of the portion of the workpiece inspected.

In one embodiment, a system for inspecting a workpiece is provided. The system includes a support surface, and at least one laser, such as a line laser, carried by the support surface and directed towards the workpiece at an oblique angle such that at least a portion of the workpiece is illuminated by the laser. The system also includes a camera, such as a charge coupled device, carried by the support surface and capable of capturing reflections from the workpiece, as well as a translation device capable of traveling proximate to the workpiece, wherein the support surface is coupled to the translation device such that the laser and the camera are capable of traveling along the workpiece. Furthermore, the system includes a data acquisition system capable of communicating with the camera such that the data acquisition system creates an image, such as a surface profile of the workpiece or a two-dimensional C-scan or B-scan, indicative of at least a portion of the workpiece based on the reflections from the workpiece.

In various aspects of the invention, the translation device travels in a generally straight direction such that the laser illuminates the workpiece in at least one stripe extending generally transverse to the direction of travel of the translation device. The at least one stripe may form the image. The system may also include at least one scan head coupled to the support surface, wherein the scan head is capable of providing positional coordinates of the translation device relative to the workpiece. The system may also include a sensor that is capable of being moved by the translation device such that the sensor simultaneously scans the workpiece while translating the laser and camera along the workpiece.

The present invention also provides a method for inspecting a workpiece. The method includes illuminating at least a portion of the workpiece with a laser, and positioning a camera proximate to the workpiece such that a field of view of the camera includes the portion of the workpiece illuminated with the laser. The method also includes translating the camera and laser along the workpiece as the laser is illuminating the workpiece, and acquiring data indicative of the workpiece by the camera. Moreover, the method includes creating an image, such as a surface profile of the workpiece or a two-dimensional C-scan or B-scan, of at least a portion of the workpiece based on the data acquired by the camera.

The method may include illuminating the workpiece with signals directed towards the workpiece at an oblique angle, or illuminating the workpiece with signals disposed in a line. The method could include translating the laser and camera in a generally straight direction such that the laser illuminates the workpiece in at least one stripe extending generally transverse to the direction in which the laser and camera are translated. The method may also include providing positional coordinates of the portion of the workpiece that is illuminated. In addition, the method may include simultaneously scanning the workpiece with a sensor proximate to the workpiece while translating the laser and camera along the workpiece. The method may further include communicating the data acquired by the camera to a data acquisition system.

The present invention therefore provides an inspection system that is capable of providing accurate and reliable images of a workpiece inspected. The inspection system is also efficient, which reduces downtime and operational and maintenance costs. The inspection system incorporates a laser and camera that dynamically generate data indicative of the surface profile of the workpiece inspected. The data generated by the camera and laser is capable of being used to create C-scan and B-scan images that are useful in analyzing the workpiece inspected. The inspection system is advantageously portable so that it may be used in a variety of locations and even remotely from a central inspection location.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
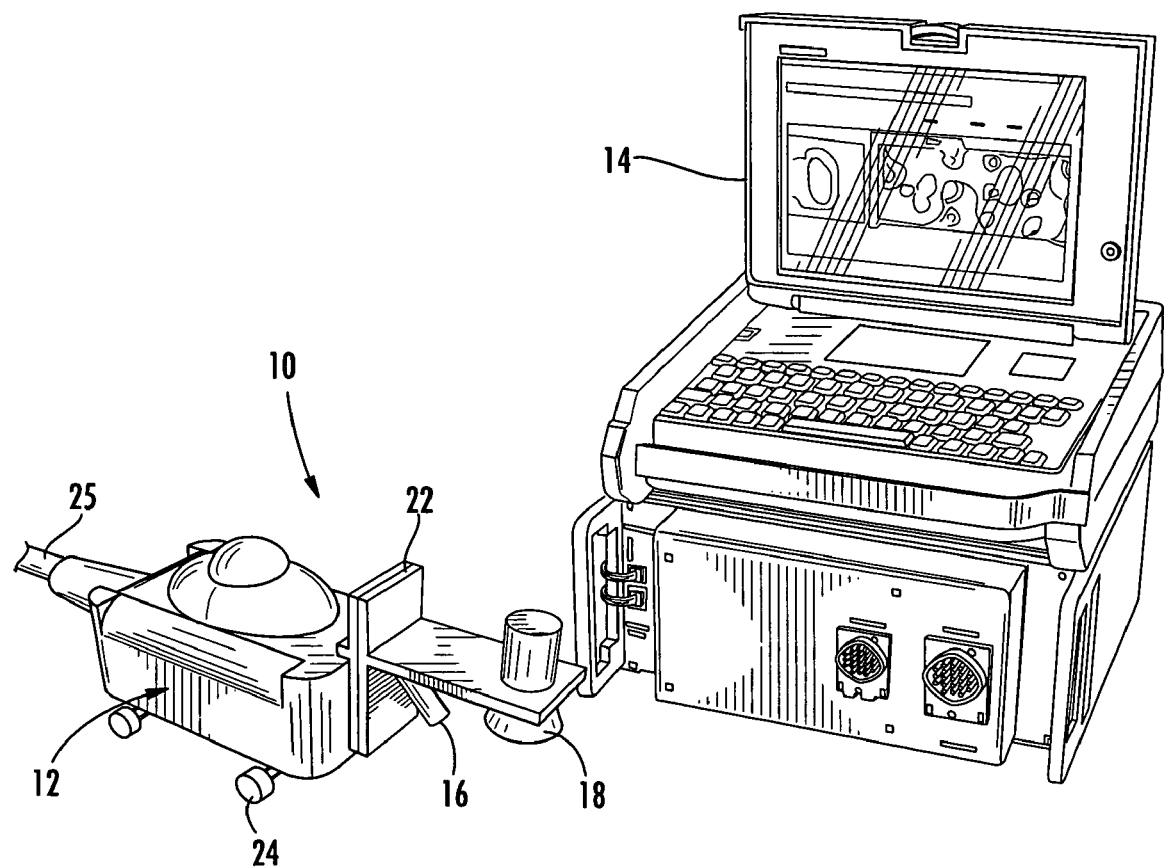
FIG. 1 is a perspective view of an inspection system according to one embodiment of the present invention.
Figure 2:
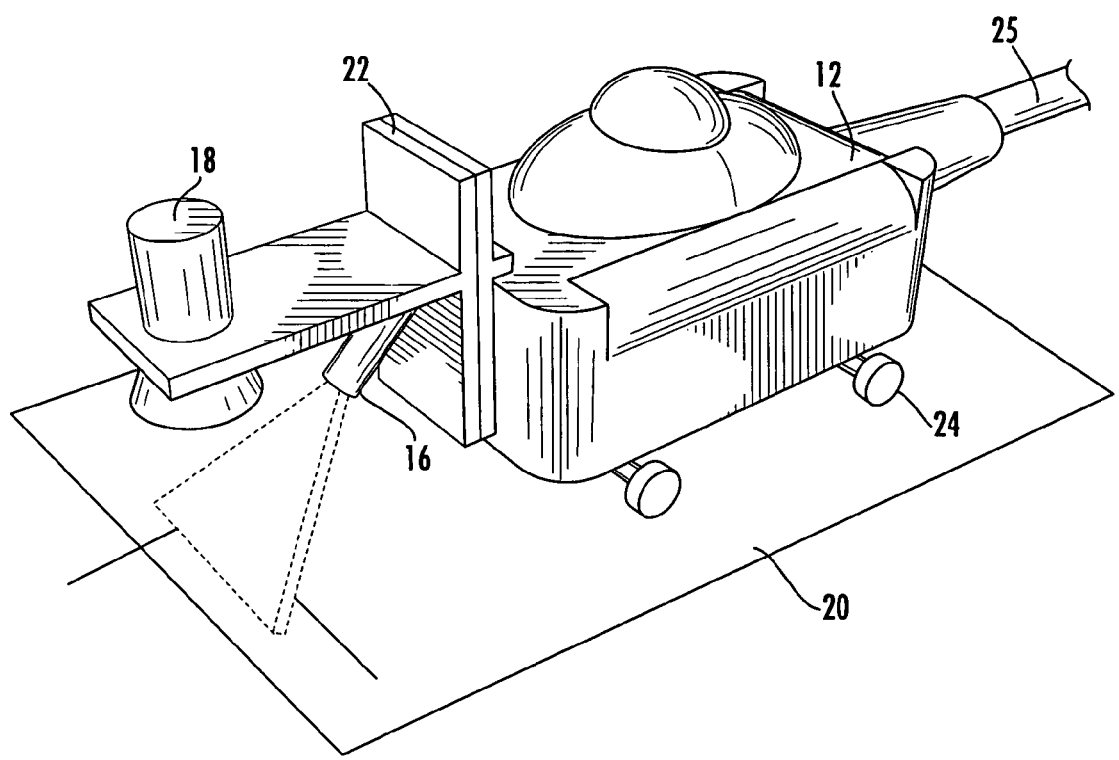
FIG. 2 is a perspective view of an inspection device employing a laser and camera, according to one embodiment of the present invention, inspecting a workpiece.

Referring now to the drawings and, in particular to FIGS. 1-2, there is shown an inspection system 10. The inspection system 10 includes a scan head 12 having a laser 16 and camera 18 coupled thereto, as well as a data acquisition system 14. As the laser 16 and camera 18 are moved along a workpiece 20, data is collected by the camera and communicated to the data acquisition system 14 for processing. Typically, as the scan head 12 moves the laser 16 proximate to the workpiece 20, the data acquisition system 14 generates topographical images of the surface of the workpiece to map the laser's response. The inspection system 10 could be used to inspect any number of workpieces 20 in a variety of industries where inspection of the workpiece is required, such as in the aircraft, automotive, construction, or manufacturing industries. For example, the inspection system 10 is particularly useful for inspecting the surface profile of a portion of an aircraft skin that has been removed by machining or grind-out.

The laser 16 illustrated in FIGS. 1-2 is a line laser, as known to those skilled in the art. The laser 16 generates a light signal that is reflective from the surface of the workpiece 20. The laser 16 generates a stripe of light when directed at an oblique angle onto the workpiece 20, where the oblique angle is typically between 20 and 90 degrees from horizontal, although any desired angle could be used. As the laser 16 is moved along the workpiece 20, the stripe of light is oriented perpendicular to the direction of travel and creates continuous stripes of light. The continuous stripes of light are reflected from the workpiece 20 and captured by the camera 16. The camera 18 is a charge coupled device (CCD) camera or other suitable camera for capturing the light reflected from the workpiece 20. Thus, the laser 16 could be any suitable device capable of generating a light signal that is reflective from the workpiece 20. Similarly, the camera 18 could be any device capable of capturing the light reflected from the workpiece 20 and capable of communicating with the data acquisition system 14. The field of view of the camera 18 generally includes a line along which the laser 16 illuminates the workpiece 20.

The laser 16 and camera 18 are carried by the scan head 12 through a support member 22. The support member 22 shown in FIG. 2 is "T-shaped," and is attached to the leading edge of the scan head 12 such that one portion of the support member is positioned adjacent to the scan head, while the other portion is positioned outwardly from the scan head and above the surface of the workpiece 20. The laser 16 could be attached to either portion of the support member 22, while the camera 18 is positioned on the support member such that the camera is spaced away from the scan head and above the surface of the workpiece 20. Typically, the laser 16 is attached to the support member 22 so that the light is directed at an oblique angle onto the workpiece, as well as ensuring that the camera 18 can capture light reflected from the workpiece. As such, the camera 18 is positioned on the support member 22 outwardly from the scan head 12 and generally perpendicular to the workpiece 20. Although the support member 22 shown in FIG. 2 is "T-shaped," it is understood that any suitable support member could be used to extend from the scan head 12 and carry the laser 16 and camera 18. For example, the support member 22 could be integral with the scan head 12, or could be a single member attached to the leading edge of the scan head. In addition, it is understood that the laser 16 could be positioned at various angles to generate a desired angle of reflectivity, while it is also understood that the camera 18 could be positioned to capture various angles of light reflected from the workpiece 20.

The scan head 12 is shown mounted on wheels 24 that allow the scan head to translate along the workpiece 20. The scan head 12 shown in FIG. 2 translates in a straight line while the laser 16 generates stripes of light perpendicular to the direction of travel. Although FIG. 2 illustrates the scan head 12 moving in a straight line, it is understood that the scan head could move in a curvilinear direction along the workpiece 20, such as to maneuver around fasteners or on a complex shaped workpiece. In addition, although the scan head 12 is shown mounted on wheels 24, it is understood that the scan head could translate using any technique, such as with a track assembly, skids, or other translating device.

The data acquisition system 14 is capable of generating various images of the topography of the workpiece 20, including B-scan and C-scan images of complex shaped workpieces 20 based on data collected by the camera 18. The images could be black and white, or color to demonstrate varying depths or other dimensions of a grind-out area. As known to those skilled in the art, a B-scan provides a profile or cross-sectional view of the workpiece 20. The B-scan is typically a two-dimensional view and would be beneficial for viewing the depth of a grind-out region of the workpiece 20. A C-scan image, which is known in the art as a plan view of the location and size of a portion of the workpiece 20 inspected, may also be two-dimensional, and may include data indicative of the workpiece on the surface or within the workpiece itself. The data may include, among other information, data regarding the surface profile or contour, defects, irregularities, or other imperfections in the workpiece 20. Generally, the plane of the C-scan created is parallel to the scan direction of the laser 16. Thus, as shown in FIG. 1 for example, the image shown on the data acquisition system 14 is a C-scan, which results from moving the laser 16 across a portion of the workpiece 20, so that an area of the workpiece is scanned by the laser. The C-scan may illustrate topographical information, such as the size and location of various grind-out regions on the workpiece 20.

The data acquisition system 14 typically includes a processor or other computing device operating under the control of imaging software so that any portion of the workpiece inspected may be presented on a display. It is possible to incorporate the data acquisition system 14 without a display and to instead provide a printout of the image scan, or to utilize any other technique for viewing the scan and location data. The processor could be embodied by a computer such as a desktop computer, laptop computer, or portable processing device capable of processing the data generated by the laser 16 and the camera 18 and creating an image of the scanned data that is shown on a display such as a monitor or other viewing device. The data acquisition system 14 generates images of the scans and also allows a user to store and edit previously created images. Therefore, a permanent record of the images may be kept for future use or record keeping. An example of software compatible with the data acquisition system 14 of the present invention is ImagIn software developed by The Boeing Company (the present assignee) that is currently used with a Mobile Automated Scanner (MAUS®, The Boeing Company).

In many cases, communications cable(s) 25 transmit data between the camera 18 and the data acquisition system 14. In other embodiments, the data may be transmitted between the camera 18 and the data acquisition system 14 via wireless communications. The camera 18 may be directly connected to the processor, or indirectly connected, such as via a network. In further embodiments of the present invention the data acquisition system 14 may be located proximate to the camera 18, such that remote connections between the camera and data acquisition system are not necessary.

In various embodiments of the present invention, the scan head 18 also includes encoders capable of providing positional information and/or sensors capable of detecting defects or other imperfections on the surface or within the workpiece 20. Encoders could be used concurrently with the laser 16 to provide positional information so that the portion of the workpiece 20 scanned by the laser can be accurately located. The encoders are typically carried by the scan head 12 and can provide up to three directional coordinates (i.e., x, y, and z).

Figure 4:
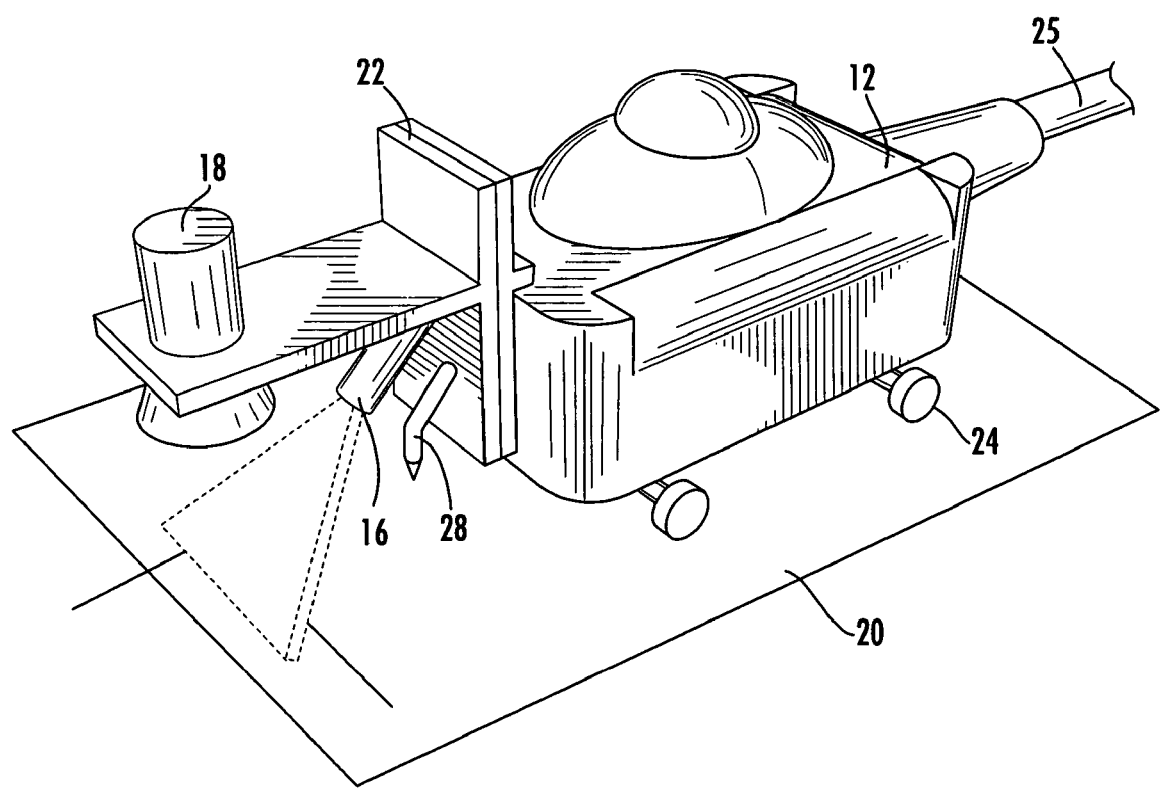
FIG. 4 is a perspective view of an inspection device employing a laser and camera, as well as a sensor, according to one embodiment of the present invention.

As shown in FIG. 4, the scan head 12 could also include a sensor 28 that is capable of detecting defects or other imperfections on or below the surface of the workpiece 20. The sensor 28 could operate concurrently with the laser 16 or separately. Thus, a routine would be utilized to switch from profiling the surface of the workpiece 20 with the laser 16 and camera 18, to inspecting the workpiece with a sensor 28 for defects or other imperfections. In the alternative, both the laser 16 and sensor 28 could be used, wherein the data acquisition system 14 can generate a single layered image or separate images for each respective method. Thus, the camera output and sensor data could be output through separate channels to the data acquisition system 14. The laser 16 and camera 18 are used in conjunction to create a sharp topographical image of the workpiece 20, while the sensor generates images of any defects or other irregularities below the surface of the workpiece.

The sensor 28 could be any suitable sensor capable of generating information for inspecting a workpiece 20. The sensor 28 is typically a non-destructive sensor, such that the sensor is capable of inspecting a workpiece 20 without harming the workpiece or requiring disassembly of the workpiece. For example, the sensor 28 could be an eddy current sensor. Single and dual frequency eddy current sensors are capable of detecting cracks and/or corrosion, particularly in metallic or other conductive workpieces 20. Other examples of sensors 28 are pulse-echo, thru-transmission, shear wave, resonance, pitch/catch, and mechanical impedance sensors. Pulse-echo, thru-transmission and shear wave sensors provide ultrasonic data, such as for thickness gauging, detection of laminar defects and porosity, and/or crack detection in the workpiece 20. Resonance, pitch/catch or mechanical impedance sensors provide indications of voids or disbonds, such as in adhesive bondlines of the workpiece 20.

The sensor 28 is typically in communication with the data acquisition system 14 to process the data accumulated by the sensor and to display the processed data. The image created could be a B-scan, or C-scan, as described above. As also described above, the sensor 28 could be in communication with the data acquisition system 14 using communication cables or with wireless technology.

Figure 3:
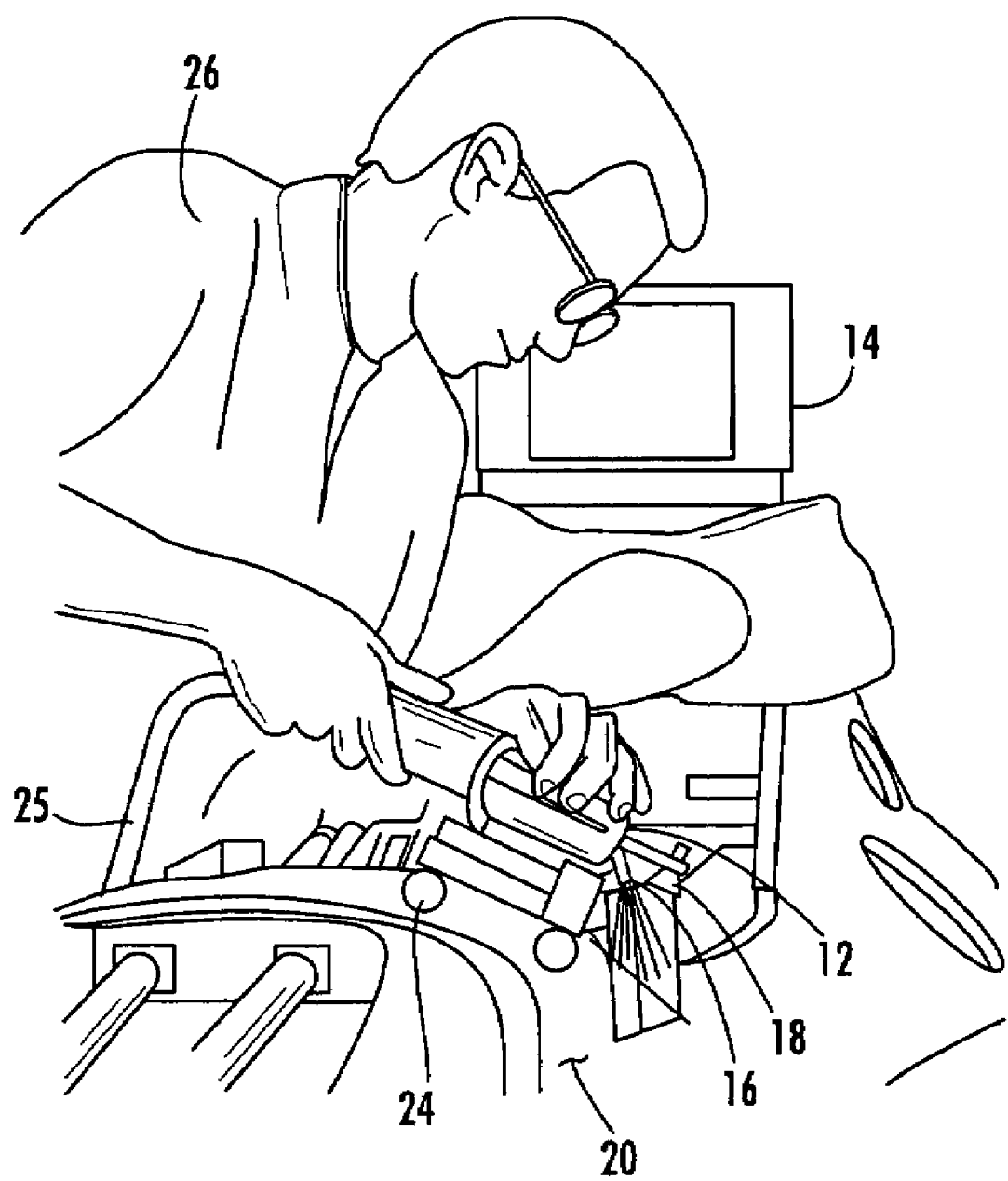
FIG. 3 is a perspective view of a user inspecting a workpiece, according to one embodiment of the present invention, using the inspection system of FIG. 1.

FIG. 3 demonstrates that the scan head 12 can be moved by a user 26 along a workpiece 20, such as an aircraft skin, to create an image of a surface profile of a portion of the workpiece. Thus, the user 26 can manually move the scan head 12, laser 16, and camera 18 collectively along the workpiece 20 in a desired direction and position on the workpiece. In general, the user 26 moves the scan head 12 in a single direction to scan a desired area of the workpiece 20. Further, the scan head 12 is generally capable of moving over a smooth, relatively rough, and/or contoured surface while directing the laser 16 at a desired orientation onto the workpiece 20, such as at an oblique angle.

Although, FIG. 3 illustrates that the scan head 12 is moved manually, it is understood that the scan head could be controlled automatically or by a combination of automated and manual movement, such as with the MAUS® system, developed by The Boeing Company (the current assignee). For example, the inspection system 10 could incorporate a track scanner or scanner having suction cups that can move along the surface of the workpiece 20.

The workpiece 20 shown in FIG. 3 is an aircraft skin. However, the term "workpiece" is not meant to be limiting, as the inspection system 10 could be used to inspect any number of parts or structures of different shapes and sizes, such as machined forgings, castings, or composite parts. In order to reflect light from the workpiece 20, it is desirable that the workpiece be capable of reflecting the light generated by the laser 16. The inspection could be performed on newly manufactured workpieces 20, or existing workpieces that are being inspected for preventative maintenance purposes.

The present invention therefore provides an inspection system 10 that is capable of providing accurate and reliable images of a workpiece 20 inspected. The inspection system 20 is also efficient, which reduces downtime and operational and maintenance costs. The inspection system 10 incorporates a laser 16 and camera 18 that dynamically generate data indicative of the surface profile of the workpiece 20 inspected. The data generated by the camera 18 and laser 16 is capable of being used to create C-scan and B-scan images that are useful in analyzing the topography of workpiece inspected. The inspection system 10 is advantageously portable so that it may be used in a variety of locations and even remotely from a central inspection location.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for inspecting a workpiece comprising:
   a support surface;
   at least one laser carried by the support surface and directed towards the workpiece at an oblique angle such that at least a portion of the workpiece is illuminated by the laser;
   a camera carried by the support surface and capable of capturing reflections from the workpiece;
   a translation device positioned adjacent to, and in direct contact with, the workpiece, wherein the support surface is coupled to the translation device such that the translation device is capable of translating the laser and the camera along the workpiece while the translation device remains in direct contact with the workpiece; and
   a data acquisition system capable of communicating with the camera such that the data acquisition system creates an image indicative of at least a portion of the workpiece based on the reflections from the workpiece.

2. A system according to claim 1, wherein the translation device is configured to translate in a generally straight direction such that the laser illuminates the workpiece in at least one stripe extending generally transverse to the direction of travel of the translation device.

3. A system according to claim 2, wherein the at least one stripe forms the image.

4. A system according to claim 1, further comprising at least one scan head coupled to the support surface, wherein the scan head is capable of providing positional coordinates of the translation device relative to the workpiece.

5. A system according to claim 1, wherein the data acquisition system creates the image in the form of a two-dimensional C-scan.

6. A system according to claim 1, wherein the data acquisition system creates the image in the form of a two-dimensional B-scan.

7. A system according to claim 1, wherein the laser comprises a line laser.

8. A system according to claim 1, wherein the camera comprises a charge coupled device.

9. A system according to claim 1, wherein the data acquisition system creates an image of a surface profile of the portion of the workpiece.

10. A system according to claim 1, further comprising a non-destructive inspection sensor coupled to the support surface and configured to obtain data indicative of a defect within the workpiece.

11. A method for inspecting a workpiece comprising:
    positioning a translation device adjacent to, and in direct contact with the workpiece, the translation device carrying a laser and a camera;
    illuminating at least a portion of the workpiece with the laser;
    positioning the camera proximate to the workpiece such that a field of view of the camera includes the portion of the workpiece illuminated with the laser;
    translating the camera and laser along the workpiece with the translation device remaining in direct contact with the workpiece as the laser is illuminating the workpiece;
    acquiring data indicative of the workpiece by the camera; and
    creating an image of at least a portion of the workpiece based on the data acquired by the camera.

12. A method according to claim 11, wherein illuminating comprises illuminating the workpiece with signals directed towards the workpiece at an oblique angle.

13. A method according to claim 11, wherein illuminating comprises illuminating the workpiece with signals disposed in a line.

14. A method according to claim 11, wherein translating comprises translating the laser and camera in a generally straight direction such that the laser illuminates the workpiece in at least one stripe extending generally transverse to the direction in which the laser and camera are translated.

15. A method according to claim 11, wherein creating an image comprises creating a two-dimensional C-scan.

16. A method according to claim 11, wherein creating an image comprises creating a two-dimensional B-scan.

17. A method according to claim 11, wherein creating an image comprises creating a surface profile of the portion of the workpiece that is illuminated.

18. A method according to claim 11, further comprising providing positional coordinates of the portion of the workpiece that is illuminated.

19. A method according to claim 11, further comprising scanning the workpiece with a non-destructive inspection sensor proximate to the workpiece in order to obtain data indicative of a defect within the workpiece.

20. A method according to claim 19, wherein scanning comprises simultaneously scanning the workpiece with the non-destructive inspection sensor while acquiring data indicative of the workpiece with the camera.

21. A method according to claim 11, further comprising communicating the data acquired by the camera to a data acquisition system.

* * * * *